United States Patent [19]

Schaeffer et al.

[11] 4,315,920
[45] Feb. 16, 1982

[54] ADENOSINE DEAMINASE INHIBITORS

[75] Inventors: Howard J. Schaeffer, Richmond, Va.; Paulo M. S. DeMiranda, Raleigh, N.C.; Gertrude B. Elion, Chapel Hill, N.C.; George H. Hitchings, Durham, N.C.

[73] Assignee: Burroughs Wellcome Co., Research Triangle Park, N.C.

[21] Appl. No.: 111,817

[22] Filed: Jan. 14, 1980

Related U.S. Application Data

[63] Continuation of Ser. No. 838,167, Sep. 30, 1977, abandoned, which is a continuation of Ser. No. 605,718, Aug. 18, 1975, abandoned.

[30] Foreign Application Priority Data

Feb. 13, 1975 [GB] United Kingdom ............... 6173/75

[51] Int. Cl.$^3$ ..................... A61K 31/70; A61K 31/52
[52] U.S. Cl. .................................. 424/180; 424/253; 424/10
[58] Field of Search .................... 424/10, 253, 180

[56] References Cited

PUBLICATIONS

Koshiura et al., Cancer Research, vol. 28, 1968, pp. 1014–1020.
Schaeffer et al., J. Med. Chem., vol. 17, No. 1, pp. 6–8 (1973).

Primary Examiner—Jerome D. Goldberg
Attorney, Agent, or Firm—Donald Brown

[57] ABSTRACT

Pharmaceutical preparations containing compounds of the formula

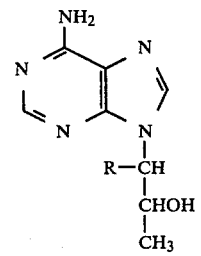

where R is alkyl of 1 to 11 carbons. The preparations are useful in inhibiting adenosine deaminase in mammals thereby providing a method for prolonging the effectiveness of pharmaceutical agents which are biologically degraded by adenosine deaminase and thus converted into other compounds.

6 Claims, 1 Drawing Figure

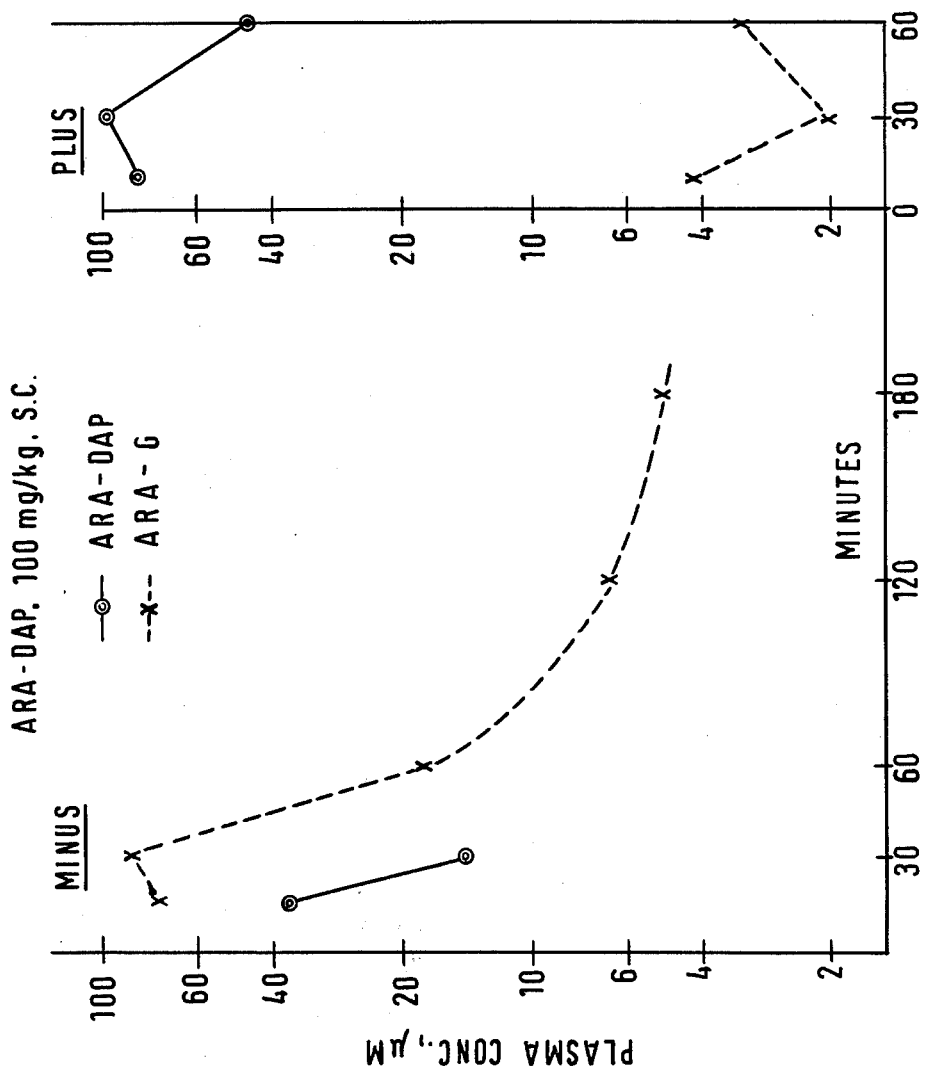

ADENOSINE DEAMINASE INHIBITORS

This is a continuation of application Ser. No. 838,167 filed Sept. 30, 1977 now abandoned which is in turn a continuation of Ser. No. 605,718 filed Aug. 18, 1975, now abandoned.

This invention relates to the inhibition of adenosine deaminase in vivo by derivatives of 9-alkyladenines and in particular by 9-(2-hydroxy-3-alkyl)adenines.

Derivatives of adenine have been reported to have cytostatic and/or antiviral activities [e.g. 9-β-D-arabinofuranosyladenine (ara-A) and 9-β-D-arabinofuranosyl-2,6-diaminopurine (ara-DAP)].

The activities of these arabinosides are influenced by the enzyme adenosine deaminase which alters the adenine or diaminopurine nucleus of these compounds in the body.

Attempts to prevent the deamination of ara-A by using a number of compounds in vivo to inhibit the enzyme and thereby the growth of tumours have, however, been disappointing. (Koshiura, R. & LePage, G. A., Cancer Research, 28, 1014–1020, 1968).

It has recently been found that 9-(2-hydroxy-3-alkyl-)adenines are effective inhibitors of adenosine deaminase in vivo. They are well absorbed, have low toxicity and relative freedom from side effects, and are capable of existence for a reasonable period of time (hours) in the body. Such adenines may therefore be used to prolong and enhance the effectiveness of antiviral agents which are sensitive to degradation by adenosine deaminase.

According to one aspect of the invention there is provided a pharmaceutical preparation which contains as an active ingredient a 9-(2-hydroxy-3-alkyl)-adenine of formula (I)

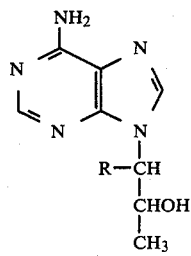

wherein R stands for an alkyl group having from 1 to 11, preferably 4 to 8, carbon atoms, or pharmaceutically acceptable salts thereof, in admixture with a pharmaceutically and physiologically acceptable carrier other than non-sterile water or solvent. Both the erythro and threo forms are active adenosine deaminase inhibitors and are included in this invention. However, the erythro isomers are generally more active than the corresponding threo isomers and are, therefore, preferable.

In a particular aspect the abovementioned preparation is preferred when it contains a compound of formula (I), as hereinbefore defined, or pharmaceutically acceptable salts thereof, in combination with a compound susceptible to adenosine deaminase action in admixture with a pharmaceutically acceptable carrier, in particular with antiviral 9-β-D-arabinofuranosyl derivatives of formula (II),

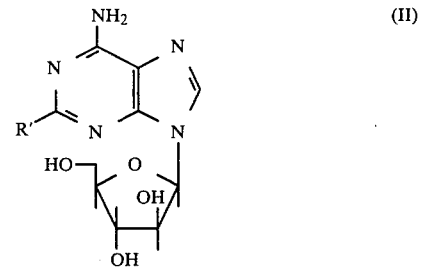

wherein R' is hydrogen, amino, loweralkylamino, or hydroxyl, or pharmaceutically acceptable salts thereof. All of the compounds of formula (II) have been shown to have anti-viral activity.

The compounds of formula (I) may conveniently be prepared by condensing 5-amino-4,6-dichloropyrimidine with the appropriate amino alcohol (Vide Schaeffer, H. J. and Schwender, C. D., *J. Med. Chem.*, 17, 6–8, 1974). The resultant pyrimidine is cyclized with triethyl orthoformate to the 6-chloropurine intermediate, which upon reaction with ammonia gives the desired 9-(2-hydroxy-3-alkyl)adenine.

The antiviral 9-β-D-arabinofuranosyl derivatives of 6-amino-purines may be prepared according to the methods disclosed in British Patent Specification No. 1,338,905. Ara-DAP may be synthesized according to the method of U.S. Pat. No. 3,758,684. The synthesis of ara-A has been disclosed by Reist, et al., *Journal of Organic Chemistry*, 27, 3274 (1962).

Pharmaceutically acceptable carriers are materials suitable for the purpose of administering the compounds and may be liquid or solid materials, which are otherwise inert or medically acceptable and are compatible with the active ingredients. Conveniently the adenosine deaminase inhibitor and antiviral drug may each be presented in admixture with a pharmaceutical carrier for administration by injection. Alternatively each of the compounds may be formulated in discrete units such as tablets, capsules or sachets for oral administration, or suppositories, each unit containing predetermined dose(s) of the 9-(2-hydroxy-3-alkyl)adenine and/or the antiviral drug. These preparations may be made by any of the methods of pharmacy and may contain as accessory ingredients any acceptable excipients, for example diluents, buffers and flavouring, binding, dispersing, lubricating and coating materials.

According to another aspect of the invention there is provided a method of making a pharmaceutical preparation wherein a 9-(2-hydroxy-3-alkyl)adenine of formula (I) or a salt thereof is admixed with a pharmaceutically acceptable carrier. In a particular aspect the above method is preferred when a 9-(2-hydroxy-3-alkyl)adenine is admixed with a compound susceptible to adenosine deaminase activity, as hereinbefore defined, and with a pharmaceutically acceptable carrier.

In a further aspect of the invention there is provided a method of treating or preventing viral infections in mammals such as mice and humans which comprises the administration of an effective antiviral amount of a 9-β-D-arabinofuranosyl derivative of a 6-aminopurine of formula (II) or a pharmaceutically acceptable salt thereof and an effective adenosine deaminase inhibition amount of a compound of formula (I) or a pharmaceutically acceptable salt thereof. By "effective adenosine deaminase inhibition amount" is meant an amount sufficient to significantly decrease the rate of in vivo deamination of the 6-amino group of a compound of formula (I).

Preferably the active ingredients are administered in formulations as described hereinbefore. As used herein the term "effective amount for anti-viral treatment" means a predetermined amount sufficient to be effective against a particular virus in vivo. The compounds of formula (II) and their pharmaceutically acceptable salts are particularly useful in treating viral infections resulting from DNA viruses, of which type vaccinia and herpes are examples.

These pharmaceutical compositions may be given parenterally, orally, or used as a suppository.

For oral administration fine powders or granules may contain diluting, dispersing and/or surface active agents. The preparations may be presented in a draught, in water, or in a syrup, in capsules or sachets in the dry state or in a non-aqueous suspension, wherein suspending agents may be included in tablets or suppositories, when binders and lubricants may be included, or in a suspension in water or a syrup. Where desirable, or necessary, flavouring, preserving, suspending, thickening or emulsifying agents can be included. Tablets and granules are preferred and these may be coated.

In treating virus infections the pharmaceutical preparation of a compound of formula (I), preferably where R is an alkyl group having 6 carbon atoms, may be administered parenterally in doses of from 1 to 50 mg/kg of body weight, preferably 5 to 25 mg/kg. This is followed by the administration of an antiviral drug such as ara-A or ara-DAP at dose levels of about 1 to 100 mg/kg of body weight. Such regimen of treatment may be repeated 2 to 4 times daily.

Alternatively the compound of formula (I) and anti-viral drug may be presented in tablet or suppository form containing 10 to 500 mg/unit preferably 50 to 200 mg/unit, most preferably 100 mg/unit of the adenosine deaminase inhibitor, and 10 to 250 mg/unit of a 9-$\beta$-D-arabinofuranosyl derivative of the 6-aminopurine.

The invention will now be described with reference to the following Examples, but is in no way to be considered limited by the same. "Adenosine deaminase inhibitor" in Examples 3, 4, 5 and 6 is a compound of formula (I) wherein R is n-$C_6H_{13}$; in Examples 7 and 8 it is a compound of formula (I) wherein R is $CH_3$; and in Examples 9 and 10 it is a compound of formula (I) wherein R is n-$C_9H_{19}$. "Anti-viral agent" in Examples 3 and 4 is ara-A, in Examples 5, 6, 9 and 10 is ara-DAP, and in Examples 7 and 8 is a compound of formula (II) wherein R' is hydroxyl.

EXAMPLE 1

A mixture of D,L-2-aminooctanoic acid (62.0 g), acetic anhydride (310 ml) and pyridine (205 ml) was heated on a steam bath for 3.5 hours. The reaction mixture was allowed to cool and then evaporated in vacuo with the addition of water to give an oily residue. This was neutralized with aqueous sodium bicarbonate (5%) and extracted with methylene chloride. The combined extracts were dried over anhydrous magnesium sulfate and evaporated in vacuo to give a dark oil (71.6 g, 95% yield). The oil was treated with concentrated hydrochloric acid (500 ml) at reflux for 2 hours. The reaction mixture was filtered through glass wool, cooled, and evaporated in vacuo to give a solid which was recrystallized from ethanol/ether to give 3-aminononan-2-one hydrochloride (52.0 g, 69% yield, m.p. 114°-116° C.).

To a solution of 3-aminononan-2-one hydrochloride (46.5 g) in methanol (200 ml) at 0° C. was slowly added sodium borohydride (26 g). The pH was maintained between 5 and 6 by the addition of glacial acetic acid. The reaction mixture was stirred overnight and then evaporated in vacuo. The residue was basicified by the addition of excess aqueous sodium hydroxide (25%) and extracted with chloroform. The combined extracts were dried over anhydrous magnesium sulfate and evaporated in vacuo. The resulting oil was distilled (b.p. 73°-76° C. at ca. 0.08 mm Hg) to give erythro-3-amino-2-nonanol (28.5 g).

A mixture of 5-amino-4,6-dichloropyrimidine (25.1 g), erythro-3-amino-2-nonanol (25.9 g), triethylamine (25 ml), and 1-butanol (450 ml) was heated at reflux under nitrogen for 24 hours. The reaction mixture was cooled and evaporated in vacuo. The resulting oil was dissolved in methanol and the solution diluted with ice to give a gummy oil which was extracted with ethyl acetate (3×300 ml). The combined extracts were washed with water, then with brine and then dried over anhydrous magnesium sulfate and evaporated in vacuo to give an oil which could be induced to crystalline by tituration in hexane (34.7 g). An analytical sample (recrystallized from benzene) melted at 119°-120.5°; however, the crude material [erythro-5-amino-4-chloro-6-(2-hydroxy-3-nonylamino)pyrimidine] could be made in the next step without further purification.

A mixture of erythro-5-amino-4-chloro-6-(2-hydroxy-3-nonylamino)pyrimidine (30.2 g), triethylorthoformate (100 ml), and ethanolsulfonic acid (180 mg) was stirred at room temperature for 3 hours. The excess triethylorthoformate was removed in vacuo and a portion (18.9 g) of the residual oil was treated with ammonia-saturated methanol (250 ml) in a stainless steel bomb at 90° C. for 22 hours. The solvent was then evaporated and the residue dissolved in tetrahydrofuran. The solution was filtered and evaporated. The residue was dissolved in ethanol which had previously been saturated with hydrochloric acid. Ether was added, precipitating a white crystalline solid, erythro-9-(2-hydroxy-3-nonyl)adenine hydrochloride (14.2 g), m.p. 178°-180° C. (recrystallized from ethanol/ether). Erythro-9-(2-hydroxy-3-nonyl)adenine may be isolated by neutralizing an aqueous solution of the hydrochloride and filtering off the precipitated product.

EXAMPLE 2

A. Following the procedure of Example 1, the following compounds are prepared:
 (1) Erythro-9-(2-hydroxy-3-butyl)adenine and its hydrochloride salt
 (2) Erythro-9-(2-hydroxy-3-dodecyl)adenine and its hydrochloride salt B. The corresponding threo compounds may be prepared following the general scheme of Example 1 except the appropriate threo-3-amino-2-alkanol is used instead of the erythro isomer. The threo isomer is made from the erythro isomer by treating the erythro-3-acetamido-2-alkanol with thionyl chloride at 0° C. for 2 hours and at 100° C. for 1.5 hours, followed by evaporation of excess thionyl chloride and acid hydrolysis of the amide.

EXAMPLE 3

Tablet (total weight 200 mg)

| Adenosine deaminase inhibitor | 25 mg |
| --- | --- |
| Lactose | 124 mg |
| Polyvinyl pyrrolidone | 5 mg |
| Corn starch | 45 mg |
| Magnesium stearate | 1 mg |

EXAMPLE 4

Tablet (total weight 300 mg)

| Adenosine deaminase inhibitor | 25 mg |
| --- | --- |
| Anti-viral agent | 100 mg |
| Lactose | 124 mg |
| Polyvinyl pyrrolidone | 5 mg |
| Corn starch | 45 mg |
| Magnesium stearate | 1 mg |

EXAMPLE 5

Injectable solution (unit dose)

| Adenosine deaminase inhibitor (hydrochloride salt thereof) | 25 mg |
| --- | --- |
| NaCl | .009 mg |
| Water for injection (qs) to | 1 ml |

EXAMPLE 6

Injectable suspension (unit dose)

| Adenosine deaminase inhibitor (hydrochloride salt thereof) | 25 mg |
| --- | --- |
| Anti-viral agent | 100 mg |
| NaCl | .009 mg |
| Water for injection (qs) to | 1 ml |

EXAMPLE 7

Capsule (unit dose)

A gelatin capsule was filled with the following ingredients:

| Adenosine deaminase inhibitor | 25 mg |
| --- | --- |
| Anti-viral agent | 100 mg |
| Lactose | 140 mg |
| Corn starch | 30 mg |
| Magnesium stearate | 3 mg |
| Fused silica | 2 mg |

EXAMPLE 8

Capsule (unit dose)

A gelatin capsule was filled with the following ingredients:

| Adenosine deaminase inhibitor | 25 mg |
| --- | --- |
| Lactose | 140 mg |
| Corn starch | 30 mg |
| Magnesium stearate | 3 mg |
| Fused silica | 2 mg |

EXAMPLE 9

A syrup suspension was prepared from the following ingredients:

| Adenosine deaminase inhibitor | 25 mg |
| --- | --- |
| Anti-viral agent | 100 mg |
| Sodium carboxymethylcellulose | 20 mg |
| Microcrystalline cellulose | 100 mg |
| Glycerin | 500 mg |
| Polysorbate 80 | 10 ml |
| Flavouring agent | 0.5 |
| Preserving agent | 0.1% |
| Sucrose syrup | 0.5 to 5 ml |

EXAMPLE 10

A syrup suspension was prepared from the following ingredients:

| Adenosine deaminase inhibitor | 25 mg |
| --- | --- |
| Sodium carboxymethylcellulose | 20 mg |
| Microcrystalline cellulose | 100 mg |
| Glycerin | 500 mg |
| Polysorbate 80 | 10 ml |
| Flavouring agent | 0.5 |
| Preserving agent | 0.1% |
| Sucrose syrup | 0.5 to 5 ml |

EXAMPLE 11

Reference should now be had to the graph of FIG. 1:

Mice were injected subcutaneously with ara-DAP (100 mg/kg) and the plasma levels (μM) of ara-DAP, and ara-G, were determined at various time intervals. Ara-DAP is degraded to ara-G when in the body. The levels of ara-DAP and ara-G in this instance are represented by the "minus" part of the graph, each point represents plasma from the pooled blood of 5 mice, sacrificed at the indicated time intervals.

In the second experiment mice were injected interperitoneally with an adenosine deaminase inhibitor, erythro-9-(2-hydroxy-3-nonyl)adenine, (25 mg/kg), followed 45 minutes later by a subcutaneous injection of ara-DAP (100 mg/kg). The plasma levels of ara-DAP and ara-G were again determined, and are represented on the graph by the "plus" part.

In both cases concentrations of the drug were determined by high pressure liquid chromatography on the Varian LCS-1010, following extraction of the plasma samples with cold perchloric acid and neutralization.

We claim:

1. The method of preventing rapid degradation of 9-β-D-arabinofuranosyladenine or a pharmaceutically acceptable salt thereof in a mammal undergoing systemic treatment with 9-β-D-arabinofuranosyladenine or a pharmaceutically acceptable salt thereof by inhibiting the conversion of 9-β-D-arabinofuranosyladine or a pharmaceutically acceptable salt thereof comprising administering to said mammal an effective degradation inhibition amount of erythro-9-(2-hydroxy-3-nonyl)adenine or a pharmaceutically acceptable salt thereof.

2. The method of claim 1 in which the mammal is administered the 9-β-D-arabinofuranosyladenine or a pharmaceutically acceptable salt thereof by oral or parenteral administration and said erythro-9-(2-hydroxy-3-nonyl)adenine or a pharmaceutically acceptable salt thereof is administered orally or parenterally.

3. The method of claim 2 in which said erythro-9-(2-hydroxy-3-nonyl)adenine or a pharmaceutically acceptable salt is administered in a tablet, in a capsule or in an injectable solution.

4. The method of claim 2 in which 9-β-D-arabinofuranosyladenine is being administered to the mammal.

5. The method of claim 2 in which the hydrochloride salt of erythro-9-(2-hydroxy-3-nonyl)adenine is administered.

6. The method of claim 4 in which the hydrochloride salt of erythro-9-(2-hydroxy-3-nonyl)adenine is administered.

* * * * *